United States Patent [19]

Thompson et al.

[11] Patent Number: 5,434,253
[45] Date of Patent: Jul. 18, 1995

[54] **DNA ENCODING *HELICOBACTER PYLORI* RECOMBINASE**

[75] Inventors: Stuart A. Thompson, Joelton; Martin J. Blaser, Nashville, both of Tenn.

[73] Assignee: Vanderbilt University, Nashville, Tenn.

[21] Appl. No.: 215,928

[22] Filed: Mar. 21, 1994

[51] Int. Cl.⁶ .................................. C07H 21/04
[52] U.S. Cl. ........................ 536/23.2; 435/252.1; 435/822; 435/252.3
[58] Field of Search ................................ 536/23.2

[56] References Cited

PUBLICATIONS

Story et al. *Science* 259: 1892–1896, 1993.
Roca and Cox *Crit. Rev. Biochem. Mol. Biol.* 25:415–56, 1990.
Labigne–Roussel et al. *J. Bacteriol.* 170(4):1704–1708, 1988.
Perez–Perez and Blaser *Infect. Immun.* 55(5):1256–1263, 1987.
Keener, S. L., McNamee, K. P., McEntee, K. (1984) "Cloning and Characterization of recA Genes from *Proteus vulgaris, Erwinia carotovora, Shigella flexneri,* and *Escherichia coli* B/r" *J. Bact.,* 160(1)153–160.

*Primary Examiner*—Robert A. Wax
*Assistant Examiner*—Kawai Lau
*Attorney, Agent, or Firm*—Needle & Rosenberg

[57] ABSTRACT

An isolated nucleic acid encoding the *Helicobacter pylori* recombinase comprising the nucleotide sequence defined in the Sequence Listing as SEQ ID NO:1 is provided. Also provided is an isolated nucleic acid that selectively hybridizes with the nucleic acid of claim 1 under stringent conditions and has at least 70% complementarity with the segment of the nucleic acid of SEQ ID NO:1 to which it hybridizes. Also provided is a mutant strain of *H. pylori* that does not express a functional recombinase (recA⁻ mutant). An immunogenic amount of the recA⁻ mutant *H. pylori* in a pharmaceutically acceptable carrier is provided. A method of immunizing a subject against infection by *H. pylori* comprises administering to the subject an immunogenic amount of mutant *H. pylori* in a carrier for the mutant.

6 Claims, 3 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
  ( A ) LENGTH: 1169 base pairs
  ( B ) TYPE: nucleic acid
  ( C ) STRANDEDNESS: double
  ( D ) TOPOLOGY: linear ( i i ) MOLECULE TYPE: DNA (genomic)

( i x ) FEATURE:
  ( A ) NAME/KEY: CDS
  ( B ) LOCATION: 349..1167

( x i ) SEQUENCE DESCRIPTION: SEQ ID NO:1:

```
TTTTTTCACT AATTTAGCCA TAGCCATTCC CAAAGCGGGA GTAGTAATCG TTCGCAATTT      60

TAGGGTATAG CCCAAAGCTG ATCGCGCTCA CATCATAAGT GTTTTTAGG GCTTCTTGGT      120

TTAGGGTTTC AATATCCAGG GCAATGTTGT GGAATGTTTT ATTTTAATG GGGCAATCTA      180

TCCAGCCAAA CTTAATCGCA TAATACATGA AAATATCATC AGCATCAGGG CTATGAGCGA      240

CACTAATCAA AGTAAAATCC TTTTGTGATA GGGTAAGTCC TTTTATTATA ATAGATTTTA      300

GGCTAGGATT TGATAGAATA AACAAATCAA ATTCAATAAG GTGATTTA ATG GCA ATA      357
                                                         Met Ala Ile
                                                           1

GAT GAA GAC AAA CAA AAA GCG ATT TCT TTA GCG ATC AAA CAA ATT GAT      405
Asp Glu Asp Lys Gln Lys Ala Ile Ser Leu Ala Ile Lys Gln Ile Asp
      5                  10                  15

AAG GTT TTT GGT AAG GGG GCG TTG GTA CGC CTT GGG GAT AAG CAA GTA      453
Lys Val Phe Gly Lys Gly Ala Leu Val Arg Leu Gly Asp Lys Gln Val
 20                  25                  30                  35

GAA AAG ATT GAC GCT ATT TCT ACA GGC TCG TTA GGA TTG GAT TTA GCT      501
Glu Lys Ile Asp Ala Ile Ser Thr Gly Ser Leu Gly Leu Asp Leu Ala
                 40                  45                  50

TTA GGG ATT GGG GGC GTT CCA AAG GGT AGG ATC ATT GAA ATT TAT GGG      549
Leu Gly Ile Gly Gly Val Pro Lys Gly Arg Ile Ile Glu Ile Tyr Gly
             55                  60                  65

CCA GAG TCA AGC GGG AAG ACC ACT CTA AGC TTG CAT ATT ATT GCA GAA      597
Pro Glu Ser Ser Gly Lys Thr Thr Leu Ser Leu His Ile Ile Ala Glu
         70                  75                  80

TGC CAA AAA AAT GGC GGC GTG TGC GCG TTC ATT GAC GCT GAA CAT GCC      645
Cys Gln Lys Asn Gly Gly Val Cys Ala Phe Ile Asp Ala Glu His Ala
     85                  90                  95

TTA GAT GTG TAT TAT GCC AAG AGG CTA GGC GTG GAT ACA GAA AAT CTA      693
Leu Asp Val Tyr Tyr Ala Lys Arg Leu Gly Val Asp Thr Glu Asn Leu
100                 105                 110                 115

CTC GTT TCC CAA CCA AGC ACG GGC GAA GAA GCC TTA GAA ATT TTA GAA      741
Leu Val Ser Gln Pro Ser Thr Gly Glu Glu Ala Leu Glu Ile Leu Glu
                120                 125                 130

ACG ATC ACC AGA AGC GGA GGG ATT GAT TTA GTG GTG GTG GAT TCG GTG      789
```

```
Thr Ile Thr Arg Ser Gly Gly Ile Asp Leu Val Val Val Asp Ser Val
            135                 140                 145

GCG GCC CTT ACG CCT AAA GCG GAG ATT GAT GGG GAT ATG GGC GAT CAG      837
Ala Ala Leu Thr Pro Lys Ala Glu Ile Asp Gly Asp Met Gly Asp Gln
        150                 155                 160

CAT GTG GGC TTG CAA GCA AGG CTT ATG AGC CAT GCG TTA AGA AAA ATC      885
His Val Gly Leu Gln Ala Arg Leu Met Ser His Ala Leu Arg Lys Ile
165                 170                 175

ACT GGT GTC TTG CAC AAG ATG AAC ACC ACT CTC ATT TTT ATC AAT CAA      933
Thr Gly Val Leu His Lys Met Asn Thr Thr Leu Ile Phe Ile Asn Gln
180                 185                 190                 195

ATA AGG ATG AAG ATC GGC ATG ACA GGT TAT GGG AGT CCA GAG ACC ACA      981
Ile Arg Met Lys Ile Gly Met Thr Gly Tyr Gly Ser Pro Glu Thr Thr
                200                 205                 210

ACC GGA GGC AAT GCC TTA AAA TTC TAT GCG AGC GTT AGG ATT GAT ATT     1029
Thr Gly Gly Asn Ala Leu Lys Phe Tyr Ala Ser Val Arg Ile Asp Ile
            215                 220                 225

AGA AGA ATC GCC GCT TTA AAA CAA AAC GAA CAG CAT ATC GGT AAT AGG     1077
Arg Arg Ile Ala Ala Leu Lys Gln Asn Glu Gln His Ile Gly Asn Arg
        230                 235                 240

GCT AAA GCT AAA GTC GTT AAA AAT AAA GTC GCT CCG CCC TTT AGA GAA     1125
Ala Lys Ala Lys Val Val Lys Asn Lys Val Ala Pro Pro Phe Arg Glu
245                 250                 255

GCG GAA TTT GAC ATC ATG TTT GGG GAA GGG ATT TCT AAA GAG             1167
Ala Glu Phe Asp Ile Met Phe Gly Glu Gly Ile Ser Lys Glu
260                 265                 270

GG                                                                   1169
```

(2) INFORMATION FOR SEQ ID NO:2:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Ile Asp Glu Asp Lys Gln Lys Ala Ile Ser Leu Ala Ile Lys
 1               5                  10                  15

Gln Ile Asp Lys Val Phe Gly Lys Gly Ala Leu Val Arg Leu Gly Asp
            20                  25                  30

Lys Gln Val Glu Lys Ile Asp Ala Ile Ser Thr Gly Ser Leu Gly Leu
 35                  40                  45

Asp Leu Ala Leu Gly Ile Gly Gly Val Pro Lys Gly Arg Ile Ile Glu
     50                  55                  60

Ile Tyr Gly Pro Glu Ser Ser Gly Lys Thr Thr Leu Ser Leu His Ile
 65                  70                  75                  80

Ile Ala Glu Cys Gln Lys Asn Gly Gly Val Cys Ala Phe Ile Asp Ala
                 85                  90                  95

Glu His Ala Leu Asp Val Tyr Tyr Ala Lys Arg Leu Gly Val Asp Thr
                100                 105                 110

Glu Asn Leu Leu Val Ser Gln Pro Ser Thr Gly Glu Glu Ala Leu Glu
            115                 120                 125

Ile Leu Glu Thr Ile Thr Arg Ser Gly Gly Ile Asp Leu Val Val Val
130                 135                 140

Asp Ser Val Ala Ala Leu Thr Pro Lys Ala Glu Ile Asp Gly Asp Met
145                 150                 155                 160

Gly Asp Gln His Val Gly Leu Gln Ala Arg Leu Met Ser His Ala Leu
                165                 170                 175
```

```
Arg Lys Ile Thr Gly Val Leu His Lys Met Asn Thr Thr Leu Ile Phe
            180                 185                 190

Ile Asn Gln Ile Arg Met Lys Ile Gly Met Thr Gly Tyr Gly Ser Pro
            195                 200                 205

Glu Thr Thr Thr Gly Gly Asn Ala Leu Lys Phe Tyr Ala Ser Val Arg
            210                 215                 220

Ile Asp Ile Arg Arg Ile Ala Ala Leu Lys Gln Asn Glu Gln His Ile
225                 230                 235                 240

Gly Asn Arg Ala Lys Ala Lys Val Val Lys Asn Lys Val Ala Pro Pro
                245                 250                 255

Phe Arg Glu Ala Glu Phe Asp Ile Met Phe Gly Glu Gly Ile Ser Lys
            260                 265                 270

Glu
```

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=X
            / note="X = Y OR F"

( x i ) SEQUENCE DESCRIPTION: SEQ ID NO:3:

```
Glu Ile Xaa Gly Pro Glu
1               5
```

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:4:

```
GARATHTYGG NCCNGA                                            16
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Asn Ala Leu Lys Phe Tyr Ala
1               5
```

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (ii) MOLECULE TYPE: oligonucleotide (xi) SEQUENCE DESCRIPTION: SEQ ID NO:6:

GCRTARAAYT TNARNGC    17

(2) INFORMATION FOR SEQ ID NO:7:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: oligonucleotide (xi) SEQUENCE DESCRIPTION: SEQ ID NO:7:

GTGAAAGCGA AAAACAAG    18

(2) INFORMATION FOR SEQ ID NO:8:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: oligonucleotide (xi) SEQUENCE DESCRIPTION: SEQ ID NO:8:

AAGAGAAGCT TTAAACCCTC C    21

DNA ENCODING *HELICOBACTER PYLORI* RECOMBINASE

This invention was made with government support under Grant No. CA 58834, awarded by the National Institutes of Health. The Government has certain rights in the invention.

BACKGROUND OF THE INVENTION

It has previously been established that genes such as recA are involved in recombination in bacteria, which contributes to intra- and intergenic variation. intragenic variation is thought to be important for bacterial growth. Bacterial RecA proteins are important in recombinational repair of damages DNA, in bacterial response to environmental stress (e.g., SOS), and also in functions such as DNA transformation and chromosomal rearrangement that are involves in bacterial pathogenesis. Nothing is known of the existence or role of recombinase in *H. pylori*, and no *H. pylori* recA gene has been identified.

*Helicobacter pylori* is the major causative agent of chronic superficial gastritis in humans, and infection with this organism is an important etiologic factor in the pathogenesis of peptic ulcer disease and possibly gastric cancer (20-22). In terms of human suffering and financial burden, *H. pylori* infection is very costly. There is no vaccine or fully effective treatment for *H. pylori* infection.

Thus there exists a need for a vaccine against *H. pylori* infection. Such a vaccine, if comprising a live attenuated bacterium should not be susceptible to reversion to the wild type. The present invention meets this need by providing the *H. pylori* recA gene and a strain of *H. pylori* that has been genetically altered so that no functional recombinase is produced.

SUMMARY OF THE INVENTION

An isolated nucleic acid encoding the *Helicobacter pylori* recombinase comprising the nucleotide sequence defined in the Sequence Listing as SEQ ID NO:1 is provided. Also provided is an isolated nucleic acid that selectively hybridizes with the nucleic acid of claim 1 under stringent conditions and is at least 70% complementary with the segment and strand of the nucleic acid of SEQ ID NO:1 to which it hybridizes. The recombinase-encoding nucleic acid and selectively hybridizing nucleic acids of the invention can be in a vector suitable for expressing the nucleic acid. The nucleic acid in a vector can be in a host suitable for expressing the nucleic acid.

Having discovered the existence of a recombinase in *H. pylori*, the invention also provides a mutant strain of *H. pylori* that does not express a functional recombinase (recA⁻ mutant). The mutant can either not express recombinase or express a non-functioning recombinase. The recA⁻ mutants are more sensitive to acidic pH than are the wild-type *H. pylori*. Thus, the invention provides a method of inducing acid sensitivity in *H. pylori*, comprising mutating the *H. pylori* so that it does not express a functional recombinase, the absence of a functioning recombinase resulting in increased acid sensitivity.

An immunogenic amount of the recA⁻ mutant *H. pylori* in a pharmaceutically acceptable carrier can be used as a vaccine. A method of immunizing a subject against infection by *H. pylori* comprises administering to the subject an immunogenic amount of mutant *H. pylori* in a carrier for the mutant.

DETAILED DESCRIPTION OF THE INVENTION

Nucleic Acids

Figure 1:
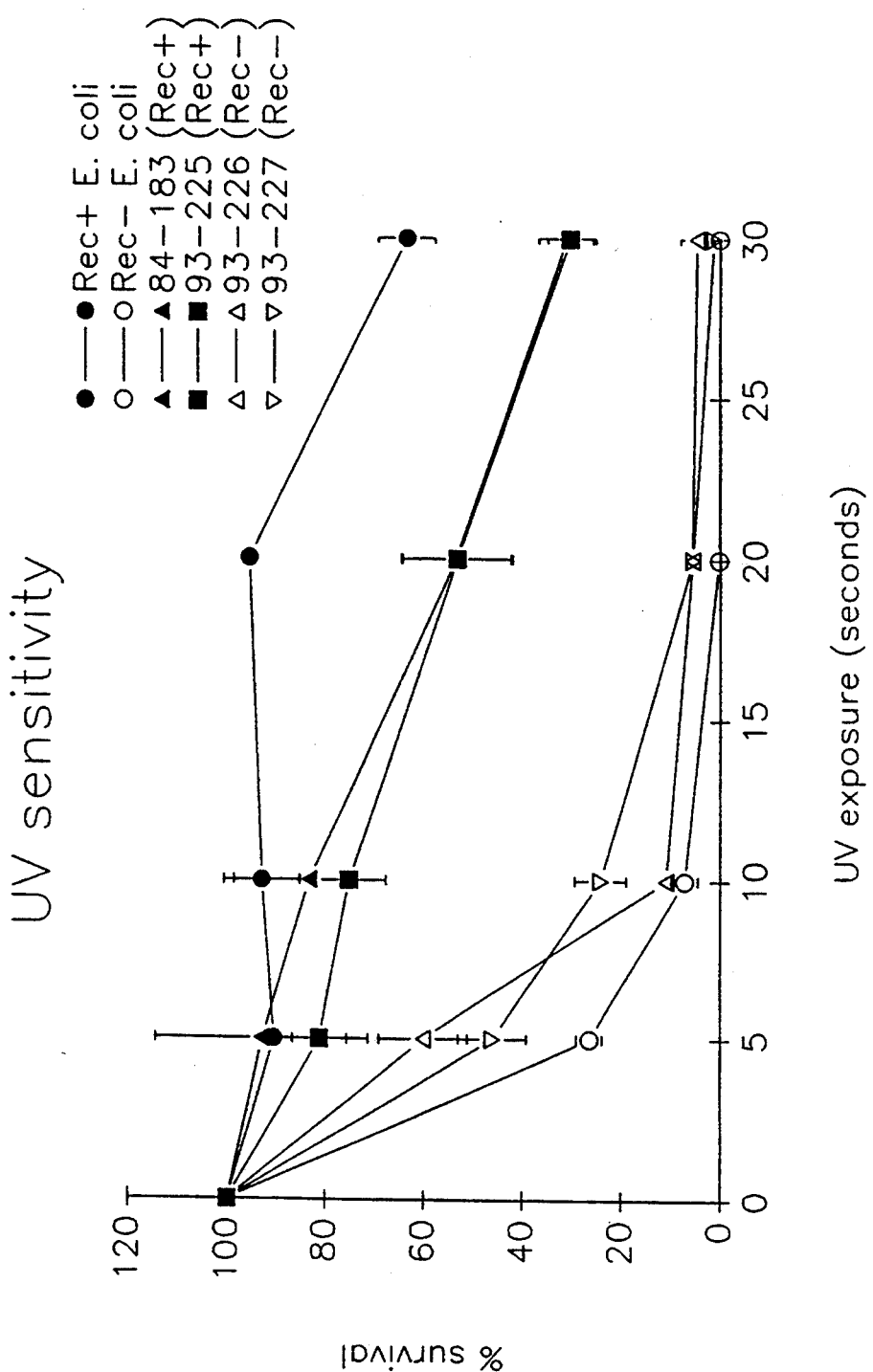
FIG. 1 shows the UV sensitivity of recA mutants.

An isolated nucleic acid encoding the *Helicobacter pylori* recombinase, comprising the nucleotide sequence defined in the Sequence Listing as SEQ ID NO:1 is provided. "Isolated" means separated from other genes of *H. pylori*. The nucleic acid of SEQ ID NO:1 is a double stranded partial sequence of the recombinase gene. Given the present disclosure of the *H. pylori* recombinase gene and partial sequence, the skilled artisan can routinely sequence the remainder of the gene.

Also provided is an isolated nucleic acid that selectively hybridizes with the nucleic acid encoding the *H. pylori* recombinase under stringent conditions and has at least 70% complementarity with the segment and strand of the nucleic acid of SEQ ID NO:1 to which it hybridizes. As used herein to describe nucleic acids, the term "selectively hybridizes" excludes the occasional randomly hybridizing nucleic acids as well as nucleic acids that encode other known recombinases. The selectively hybridizing nucleic acids can be used, for example, as probes or primers for detecting the presence of an organism that has the nucleic acid to which it hybridizes. Thus, the invention provides a method of detecting *Helicobacter pylori* infection in a subject, comprising detecting the presence of the selectively hybridizing nucleic acid in a specimen from the subject, the presence of the nucleic acid indicating infection with *Helicobacter pylori*. Alternatively, the selectively hybridizing nucleic acid can encode a polypeptide, and, can thereby be placed in a vector and host to produce the recombinase, a functionally similar recombinase, an antigenic fragment or a fragment exhibiting recombinase function.

The selectively hybridizing nucleic acids of the invention can have at least 70%, 80%, 85%, 90%, 95%, 97%, 98% and 99% complementarity with the segment and strand of the sequence to which it hybridizes. The nucleic acids can be at least 18, 50, 100, 150, 200, 300, 500, 750, 1000, 2000, 3000 or 4000 nucleotides in length. Thus, the nucleic acid can be an alternative coding sequence for the recombinase, or can be used as a probe or primer for detecting the presence *H. pylori*. If used as primers, the invention provides compositions including at least two nucleic acids which selectively hybridize with different regions so as to amplify a desired region. Depending on the length of the probe or primer, it can range between 70% complementary bases and full complementarity and still hybridize under stringent conditions. For example, for the purpose of diagnosing the presence of *H. pylori*, the degree of complementarity between the hybridizing nucleic acid (probe or primer) and the sequence to which it hybridizes (*H. pylori* DNA from a sample) should be at least enough to exclude hybridization with a nucleic acid from related bacterium. Thus, a nucleic acid that selectively hybridizes with a *H. pylori* recombinase coding sequence will not selectively hybridize under stringent conditions with a nucleic acid for a recombinase of another species, and vice versa. The invention provides examples of these nucleic acids of *H. pylori*, so that the degree of complementarity required to distinguish selectively hybridizing from nonselectively hybridizing nucleic acids under stringent conditions can be clearly determined for each nucleic acid. It should also be clear that a selectively hybridizing nucleic acid will not hybridize with nucleic acids encoding unrelated proteins.

"Stringent conditions" refers to the washing conditions used in a hybridization protocol. In general, the washing conditions should be a combination of temperature and salt concentration chosen so that the denaturation temperature is approximately 5°-20° C. below the calculated $T_m$ of the hybrid under study. The temperature and salt conditions are readily determined empirically in preliminary experiments in which samples of reference DNA immobilized on filters are hybridized to the probe or protein coding nucleic acid of interest and then washed under conditions of different stringencies. For example, the 470 bp recA PCR fragment (described below) is used as a specific radiolabeled probe for *H. pylori* recA by performing hybridizations at 68° C. in the presence of 5× SSPE (12), then removing non-specific hybrids by high-stringency washes of 0.1× SSPE at 68° C. as described in reference 12, chapter 9. Hybridizations with oligonucleotide probes shorter than 18 nucleotides in length are done at 5°-10° C. below the estimated $T_m$ in 6× SSPE, then washed at the same temperature in 2× SSPE as described in reference 12, chapter 11. The $T_m$ of such an oligonucleotide can be estimated by allowing 2° C. for each A or T nucleotide, and 4° C. for each G or C. An 18 nucleotide probe of 50% G+C would, therefore, have an approximate $T_m$ of 54° C.

One skilled in the art can readily obtain the nucleic acids of the present invention using routine methods to synthesize a full gene as well as shorter nucleotide fragments. For example, techniques for obtaining nucleic acids such as those provided in the Sequence Listing are specifically provided in the application. Furthermore, additional methods are provided in the art that can be utilized without significant modification. Ferretti et al. (*Proc. Natl. Acad. Sci.* 82:599-603 (1986)) and Wosnick et al. (*Gene* 76:153-160 (1989)) show routine methods to synthesize a gene of known sequence. More specifically, Ferretti et al. teach the synthesis of a 1057 base pair synthetic bovine rhodopsin-gene from synthetic oligonucleotides. The synthesized gene was faithful to the known sequence (first sentence, page 603), demonstrating the reliability of this method of gene synthesis. Additionally, Wosnick et al. teach the synthesis of a maize glutathione-transferase (GST) gene using an efficient, one-step annealing/ligation protocol. This technique also produced a complete synthetic gene with 100% fidelity, which demonstrates the routine nature of this protocol.

Readily available methods can be used to determine the rest of the sequence of the recombinase gene. For example, the 3' end of the recA gene can be cloned and its DNA sequence determined in a manner similar to that used in isolating the 5' end of the gene. Namely, a specific chromosomal DNA fragment can be predicted to contain the 3' end of the recA gene by Southern hybridization analysis. This fragment can then be isolated from a genomic library of *H. pylori* 84-183 DNA prepared in λZAPII using chromosomal DNA digested with the desired restriction enzyme. Identification and isolation of the desired recombinant clone would be achieved following hybridization with a recA-specific probe as described above. DNA sequence analysis of this clone would provide the sequence of the remainder of the recA gene.

Vectors and Hosts

The recombinase-encoding nucleic acid and selectively hybridizing nucleic acids of the invention can be in a vector suitable for expressing the nucleic acid. The nucleic acid in a vector can be in a host suitable for expressing the nucleic acid.

There are numerous *E. coli* expression vectors known to one of ordinary skill in the art useful for the expression of the antigen. Other microbial hosts suitable for use include bacilli, such as *Bacillus subtilus*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, the carboxy-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MFα-1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary cell line using a methotrexate resistance-encoding vector. Presence of the vector DNA in transformed cells can be confirmed by Southern analysis and production of an RNA corresponding to the antigen coding sequence can be confirmed by Northern analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the DNA segments of interest can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Alternative vectors for the expression of antigen in mammalian cells, those similar to those developed for the expression of human gamma-interferon, tissue plasminogen activator, clotting Factor VIII, hepatitis B virus surface antigen, protease NexinI, and eosinophil major basic protein, can be employed. Further, the vector can include CMV promoter sequences and a polyadenylation signal available for expression of inserted DNAs in mammalian cells (such as COS7).

The DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Mutant Organism

Having discovered the existence of a recombinase in *H. pylori*, the invention also provides a genetically altered mutant strain of *H. pylori* that does not express a functional recombinase (recA− mutant). The mutant can either not express recombinase or express a nonfunctioning recombinase. In one example, the mutant *H. pylori* strain is obtained by making an insertion substitution mutation in the coding sequence for the recombinase as described in the Examples. Since the present invention provides the nucleic acid encoding the recombinase, other methods of mutating the coding sequence of the recombinase can be used to obtain other mutant strains as contemplated herein.

An example of the mutant *H. pylori* strain of the present invention is designated 93-226 and is deposited with the American Type Culture Collection (1230 Parklawn Drive, Rockville, Md. 20852) under ATCC Accession Number 55541. A further example of a mutant *H. pylori* strain of the present invention is designated 93-227 and is deposited with the American Type Culture Collection under ATCC Accession Number 55542.

Additional mutants can be prepared, for example, by inserting a nucleic acid in the recA gene or deleting a portion of the recA gene so as to render the gene nonfunctional or protein produced in such low amounts that the organism is non-infectious or attenuated. Furthermore, by providing the nucleotide sequence for the nucleic acid encoding the recombinase, the present invention permits the making of specific point mutations having the desired effect. The deletion, insertion or substitution mutations can be made in either the regulatory or coding region to prevent transcription or translation or to render the transcribed and translated product nonfunctional.

One such approach to the construction of a deletion or insertion mutant is via the Donnenberg method (Donnenberg and Kaper *Infect. Immun.* 4310–4317, 1991). A deletion in recA is created by deleting a restriction fragment and religating the clone. This mutant is cloned into suicide vector pILL570. The sacB gene of *Bacillus subtilis* is also cloned into the suicide vector to provide a conditionally lethal phenotype. This construct is transformed into *H. pylori* by electroporation, and transformants selected by spectinomycin resistance. The merodiploid strain which contains the suicide vector and the mutated version of the recA gene are exposed to sucrose to directly select for organisms that have undergone a second recombination, resulting in the loss of the vector. These and other well known methods of making mutations can be applied to the nucleic acids provided herein to obtain other desired mutations. Included are insertional mutagenesis as described in reference 8, as well as linker-scanning mutagenesis (23) and site-directed mutagenesis (24).

Non-isogenic mutants are also within the scope of the invention. For example, a live attenuated *H. pylori* that is also a recA− mutant according to the present invention, is provided. A recA−cagA− mutant strain is constructed, for example, by insertion mutation of both the cagA and recA genes, according to the methods taught herein and taught in U.S. application Ser. No. 08/053,614, which describes the generation of a cagA (referred to therein as tagA) mutant. A recA−vacA− mutant strain is constructed, for example, by insertion mutation of both the recA and vacA genes, according to the methods taught herein. A recA−cagA− vacA− mutant strain is constructed, for example, by insertion mutation of the recA, cagA and vacA genes, according to the methods taught herein for recA and vacA, and taught in U.S. application Ser. No. 08/053,614, which describes the generation of a cagA mutant. Any of the well known methods of mutating a gene can be used in the present invention to generate *H. pylori* mutant strains. The strains can be tested as provided for immunogenicity.

The recA⁻ mutants are more sensitive to acidic pH than are the wild-type *H. pylori*. Thus, the invention provides a method of inducing acid sensitivity in *H. pylori*, comprising mutating the *H. pylori* so that it does not express a functional recombinase. The absence of a functioning recombinase results in increased acid sensitivity. Such a method of generating a mutant *H. pylori* and measuring its acid sensitivity are provided in the Examples.

Vaccines

An immunogenic amount of the recA⁻ mutant *H. pylori* in a pharmaceutically acceptable carrier can be used as a vaccine. A method of immunizing a subject against infection by *H. pylori* comprises administering to the subject an immunogenic amount of mutant *H. pylori* in a carrier for the mutant.

The recA⁻ mutants are well suited for use as a vaccine. Because of the increased acid sensitivity of the mutants, the mutant can be introduced into the stomach of the subject and remain long enough to stimulate an immune response, but will die before significant disease resulting from infection occurs.

Furthermore, because recombinase plays a role in genetic variability, the mutants of the invention are genetically more stable than wild-type *H. pylori*. Thus, a live attenuated *H. pylori* that is also a recA⁻ mutant according to the present invention, is less likely to revert to virulence than a recA⁺ *H. pylori*.

Determining immunogenicity

The isolated mutant strains of the invention can be tested to determine their immunogenicity. Briefly, various concentrations of a putative immunogen are prepared and administered to an animal and the immunological response (e.g., the production of antibodies or cell mediated immunity) of an animal to each concentration is determined. The amounts of antigen administered depend on the subject, e.g. a human or a guinea pig, the condition of the subject, the size of the subject, etc. Thereafter, an animal so inoculated with the strain can be exposed to the bacterium to test the potential vaccine effect of the specific immunogenic protein or fragment.

For example, a well-established model is that of gnotobiotic piglets, in which the recA mutant strain is first fed to the piglets. After a suitable interval, the clearance of the vaccine strain is evaluated. Next, this piglet is challenged with the wild-type strain and the presence or absence of infection is ascertained (25,26).

Once immunogenicity is established as described above, immunogenic amounts of the antigen can be determined using standard procedures. Briefly, immunogenic amounts of a recA⁻ mutant of the invention can be determined using standard procedures. Briefly, various concentrations of the recA⁻ mutant are prepared, administered to an animal and the immunological response (e.g., the production of antibodies) of an animal to each concentration is determined.

Pharmaceutically acceptable carrier

The pharmaceutically acceptable carrier in the vaccine of the instant invention can comprise saline or other suitable carriers (Arnon, R. (Ed.) *Synthetic Vaccines* I:83–92, CRC Press, Inc., Boca Raton, Fla., 1987). An adjuvant can also be a part of the carrier of the vaccine, in which case it can be selected by standard criteria based on the antigen used, the mode of administration and the subject (Arnon, R. (Ed.), 1987). Methods of administration can be by oral or sublingual means, or by injection, depending on the particular vaccine used and the subject to whom it is administered.

It can be appreciated from the above that the vaccine can be used as a prophylactic or a therapeutic modality, for example, by inducing a therapeutic immune response. Thus, the invention provides methods of preventing or treating *H. pylori* infection and the associated diseases by administering the vaccine to a subject.

EXAMPLES

Strains and growth conditions.

Strains and plasmids used in this study are listed in Table 1. *E. coli* were routinely grown in LB broth or agar (12) supplemented with carbenicillin (100 μg/ml), kanamycin (30 μg/ml), and/or chloramphenicol (30 μg/ml) when appropriate. *H. pylori* strains were grown on blood agar plates at 37° C. in an atmosphere of 5% $CO_2$/95% air. Antibiotic-resistant *H. pylori* were selected with 30 μg/ml kanamycin or 15 μg/ml chloramphenicol.

TABLE 1

Strains/plasmids used in this study.

| Strain/plasmid | Relevant genotype | Reference |
|---|---|---|
| *E. coli* | | |
| Y1089 | recA⁺ | (19) |
| DH5αMCR | recA1 | (6) |
| *H. pylori* | | |
| 84–183(ATCC 53726) | recA⁺ | (9) |
| 93–225 | recA⁺ cagA::kan | this study |
| 93–226(ATCC 55541) | recA::kan | this study |
| 93–227(ATCC 55542) | recA::chlor | this study |
| Plasmids | | |
| pSAT101 | recA (5' end) | this study |

DNA techniques.

Restriction enzymes and Klenow fragment of *E. coli* DNA polymerase I were purchased either from New England Biolabs (Beverly, Mass.) or from Promega (Madison, Wis.), and were used according to manufacturer's directions. *H. pylori* chromosomal DNA was prepared as previously described (14). Hybridizations were done as previously described (2), using $^{32}$P-labeled probes made by random-priming (4) with a kit from Boehringer-Mannhelm Biochemical Corp. (Indianapolis, Ind.). DNA sequencing was done on double-stranded templates (7) by the method of Sanger et al. (13) using a Sequenase 2.0 kit (U.S. Biochemical Corp., Cleveland, Ohio).

DNA sequence resulting from unambiguous reading of both strands was compiled using the Staden alignment programs (16). Computer analyses of DNA and protein sequences were performed using the GCG programs (3). Database similarity searches were performed via e-mail to the National Center for Biotechnology Information using the BLASTX algorithm (1,5).

PCR amplification and cloning of *H. pylori* recA.

Degenerate PCR primers were designed based on conserved amino acid sequences of bacterial recA genes (11) and were synthesized at the Vanderbilt University DNA Core Facility in a Milligen 7500 DNA synthesizer. Primer Rec1F was based on the amino acid sequence EI(Y/F)GPE (SEQ ID NO:3) and had the sequence 5' GARATHTWYGGNCCNGA 3' (SEQ ID NO:4). Primer Rec2R was based on the reverse complement of the amino acid sequence NALKFYA (SEQ ID NO:5) and had the sequence 5' GCRTARAAYTT-NARNGC 3' (SEQ ID NO:6). Thermocycler parameters were as follows: 1 minute at 94° C. (denaturation); 2 minute ramp to 37° C., followed by 2 min. at 37° C.

(primer annealing); 2 minute ramp to 60° C., followed by 2 min. at 60° C. (extension).

Degenerate PCR on *H. pylori* 84–183 chromosomal DNA using these primers resulted in the amplification of 4 products, ranging in size from 350 bp to 800 bp. One of these was approximately the expected size (~470 bp), co-migrated with the product amplified from *E. coli* DH5α MCR, and was subsequently subcloned into the pT7Blue T-vector. A BLAST search of GenBank with the sequence of the subcloned PCR product verified that it was a portion of the *H. pylori* recA gene.

λZAPII was purchased from Stratagene (LaJolla, Calif.) and was used, according to the manufacture's instructions, to prepare a genomic library from *H. pylori* 84–183. Chromosomal DNA from 84–183 was partially digested with AluI. Digested DNA in the size range of 2–7 kb was purified and ligated with EcoRI linkers. The resulting fragments were ligated with EcoRI-digested, alkaline phosphatase-treated λZAPII arms and packaged into bacteriophage A heads with Gigapack extracts (Stratagene).

To isolate the entire recA gene, a λZAPII library previously constructed from partially AluI-digested *H. pylori* 84–183 chromosomal DNA was screened. The PCR-amplified recA fragment was used as probe and identified three plaques containing recA sequences. Each was excised to a pBluescript plasmid (Stratagene) by the addition of helper phage. Restriction analysis of these clones revealed that all contained identical 2.3 kb inserts. One of these was designated pSAT101 and was subjected to DNA sequence analysis (SEQ ID NO:1). One end of the insert was within an 820 bp open reading frame (ORF). The deduced amino acid sequence of this ORF showed high similarity to bacterial RecA proteins when used in a BLAST search of GenBank.

Features of *H. pylori* recA sequence.

The partial DNA and protein sequences reported in SEQ ID NO:1 and SEQ ID NO:2, respectively, have many features typical of bacterial recA sequences. Consensus −35 and −10 promoter elements begin at positions 263 (TTGTGA) and 287 (TATAAT), respectively. The first ATG initiation codon of the following ORF is preceded by a ribosome binding site (RBS) located at position 339 (AGG). The ORF contained on pSAT101 is 273 codons in length and does not contain a termination codon. This ORF, therefore, is approximately 80% the length of a typical bacterial recA gene (352 codons for *E. coli* recA). Story et al. (17) identified amino acid residues that are highly conserved or invariant in bacterial RecA proteins and related bacteriophage and yeast recombination proteins. All of these residues were present and in the predicted location in the deduced amino acid sequence of the pSAT101 ORF (SEQ ID NO:2). The residues identified are glycine[67], lysine[73], threonine[74], aspartic acid[95], glutamic acid[97], tyrosine[104], aspartic acid[145], serine[146], asparigine[194], glutamine[195], and glycine[213].

Mutagenesis of cloned *H. pylori* recA gene.

To confirm that this gene was in fact *H. pylori* recA, isogenic mutants were constructed in which the recA coding sequence had been interrupted by antibiotic resistance markers. Fragments containing the kanamycin- and chloramphenicol-resistance genes were prepared as follows. The chloramphenicol marker from pRY109 (18) was subcloned into the PstI site of pBluescript to create pBS103, then isolated following HincII and SmaI digestion. The recA-containing plasmid pSAT101 was linearized at a unique Sty I site, located within codon 31 of the recA ORF. Following fill-in of these ends by Klenow enzyme, this molecule was ligated to either the kanamycin- or chloramphenicol-resistance fragments. After transformation into *E. coli* DH5αMCR and selection on appropriate antibiotics (carbenicillin and kanamycin, or carbenicillin and chloramphenicol), one colony was chosen from each ligation (pSAT101::kan and pSAT101::chlor).

Electroporation of *H. pylori* 84–183.

The plasmids pSAT101::kan and pSAT101::chlor were used as donor DNAs in electroporation of *H. pylori* 84–183. *H. pylori* 84–183 cells were scraped from 4 blood agar plates (24 hours old) and washed as described previously (15); this provided the cells for use in five electroporations. Approximately 1 μg of supercoiled donor plasmid was mixed with the washed cells and placed in a Gene-Pulser (Bio-Rad, Melville, N.Y.) and electroporated at 2500 V, 200Ω, and 25 μF (15). Cells were then plated onto blood agar plates without antibiotics. Following overnight growth at 37° C., the entire plate was swabbed and streaked onto blood agar plates containing either kanamycin or chloramphenicol (see above). Antibiotic-resistant colonies were harvested after 3 days growth at 37° C.

Following electroporation and plating on selective medium, 10 kanamycin-resistant colonies and one chloramphenicol-resistant colony were recovered. One kanamycin-resistant colony (93–226) and one chloramphenicol-resistant colony (93–227) were characterized further by Southern hybridization with probes for the recA gene, kanamycin- or chloramphenicol-resistance markers, and the pBluescript vector. As expected, insertion of the kanamycin-resistance marker in strain 93–226 caused a 1.4 kb increase in the size of the recA-containing SacI restriction fragment. Similarly, insertion of the chloramphenicol-resistance marker caused a 1.1 kb increase in the recA-containing SspI fragment of strain 93–227. In neither strain was the insertion of the antibiotic-resistance marker accompanied by insertion of vector sequences.

UV sensitivity of recA− *H. pylori*.

To test for loss of activity of the *H. pylori* recA protein, the sensitivities of wild-type and recA− strains to irradiation with ultraviolet light were assayed. Approximately 100 and 1000 CFU of bacteria were plated onto blood agar plates, which were then exposed to 254 nm UV light for varying amounts of time (FIG. 1). RecA+ and RecA− *E. coli* strains were used as controls in this experiment, as was an *H. pylori* 84–183 derivative in which a kanamycin-resistance marker had been inserted into the cagA locus. Survival of RecA+ *E. coli* remained high throughout the UV exposures of this experiment, while RecA− *E. coli* were killed rapidly. RecA+ *H. pylori* strains 84–183 and 93–225 were similar in their susceptibilities to UV, verifying that kanamycin-resistance per se had no effect on survival. Both RecA+ *H. pylori* strains were somewhat more sensitive to killing by UV than RecA+ *E. coli*. Survival of both RecA− mutant strains 93–226 and 93–227 was similar to that seen for RecA− *E. coli*. Therefore, both 93–226 and 93–227 have phenotypes consistent with loss of RecA function.

Increased sensitivity of recA mutant to low pH.

Urease-expressing *H. pylori* strains are quite resistant to acidic pH when provided with physiological concentrations of urea. To test whether mutation of the recA gene affected the ability of *H. pylori* to survive incubation in low pH, the assay of Perez-Perez et al. (10) was used. Phosphate buffers of different pH were prepared as follows. The pH of 0.2M dibasic sodium phosphate was adjusted to 7.0 with 0.2M monobasic sodium phosphate, or adjusted to 4.0 or 3.3 with 0.1M citric acid. Suspensions of the wild-type strain 84–183 and its isogenic recA mutant 93–226 were incubated in parallel conditions of pH 7.0, pH 4.0, and pH 3.3, either in the presence or absence of 10 mM urea. Following 1 hour incubation at 37° C., the cells were diluted in phosphate buffer (pH 7.0) and rapidly spread on blood agar plates. The number of surviving colonies was counted following five days growth on plates. The kill was determined as the log of the number of bacteria killed at pH 4.0 or 3.3 as compared to that occurring at pH 7.0.

Figure 2A:
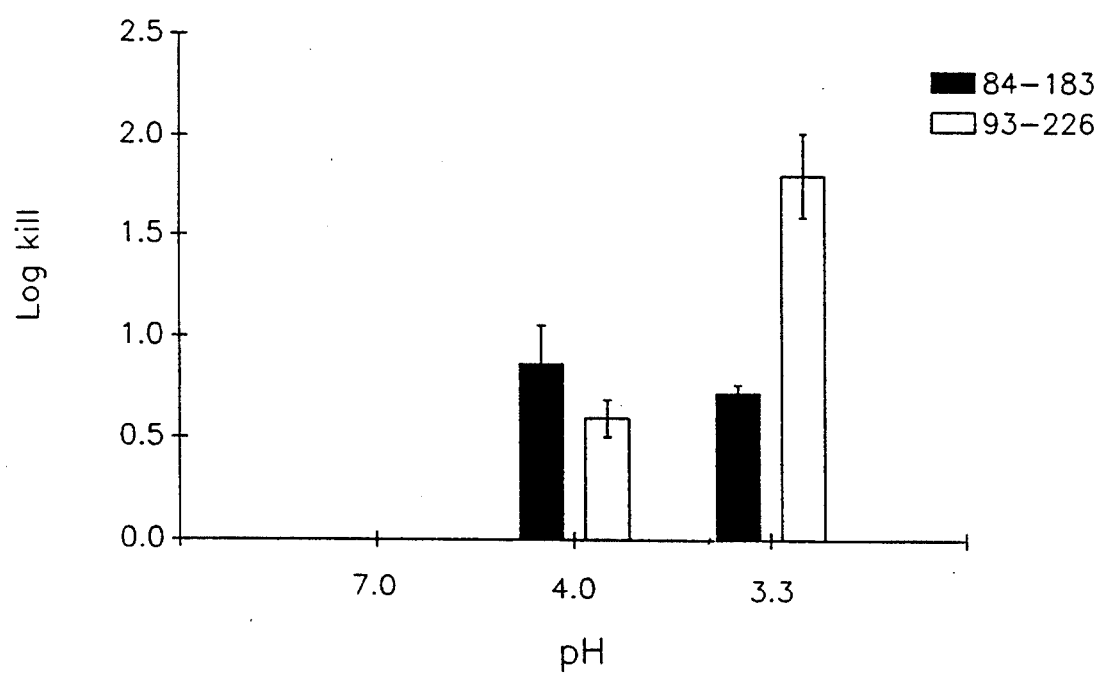
FIG. 2A shows the acid sensitivity of recA mutants in the presence of 10 mM urea.
Figure 2B:
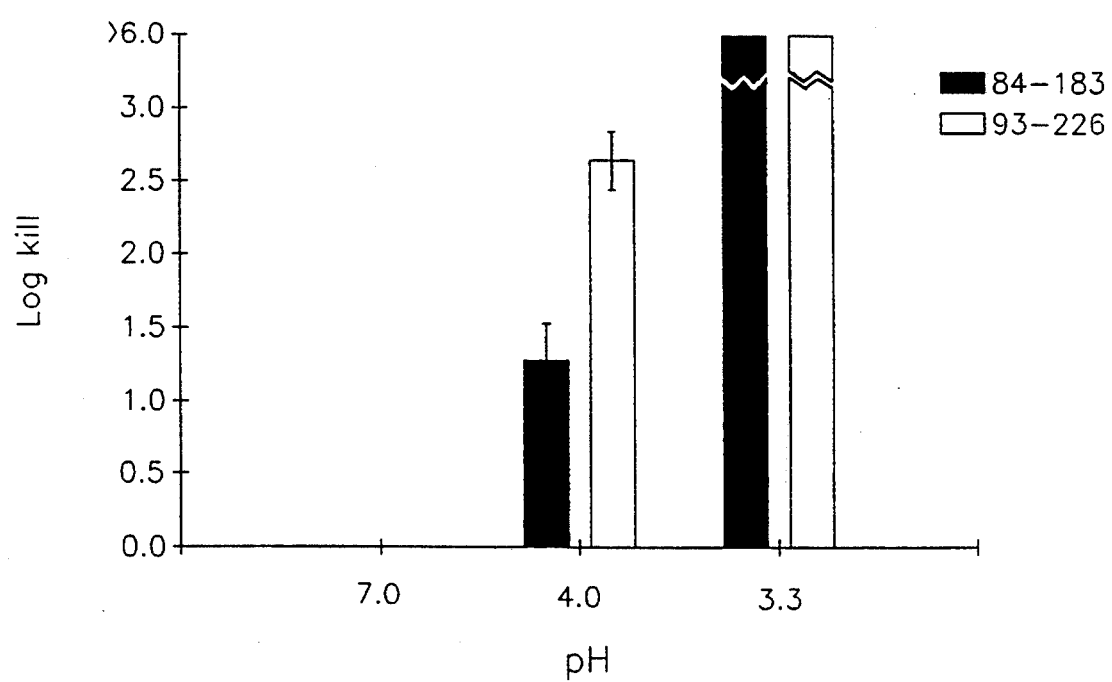
FIG. 2B shows the acid sensitivity of recA mutants in the absence of urea.

The average of the results of two such experiments is shown in FIG. 2. In the presence of urea at pH 4.0, the kill was similar for both 84–183 and 93–226. However, in the presence of urea at pH 3.3, the recA strain was killed to a level about 13 times greater than that of the wild-type strain. A similar result was seen in the absence of urea at pH 4.0, where 93–226 was killed to a level about 24 times greater than that of 84–183. Almost complete killing of both strains was observed at pH 3.3 in the absence of urea, and an accurate calculation of the difference in survival between strains was not possible. These results indicate that the recA gene product plays a role in the survival of *H. pylori* at low pH.

Generation of recA$^-$vacA$^-$ mutant.

The Donnenberg reference provides a general method of creating mutations that can be used for construction of double or triple mutants such as recAcagA, recAvacA, or recAcagAvacA. For example, a deletion in cagA or vacA would be made as described by Donnenberg and Kaper, and then a cagA or vacA mutant strain made by introducing the mutated gene into *H. pylori*. A mutated recA gene (constructed either as described herein, or as by Donnenberg) would then be introduced into the cagA or vacA mutant strain by electroporation. The recA mutation should be the last one introduced into a strain, because the recA gene product is expected to be necessary for the recombination needed to integrate the mutated sequences into the *H. pylori* chromosome.

A 1.6 kb fragment encoding the first 1236 bp of the vacA ORF plus 393 bp of upstream sequence was PCR-amplified from *H. pylori* 60190 DNA, and subcloned in pT7Blue to create pCTB8. This plasmid was partially digested with EcoRI, and ligated with a *C. coli* kanamycin (km) resistance gene (22,23). Plasmid pILL 600 was used as a source of a *Campylobacter coli* kanamycin (km) resistance gene (22,23). More specifically, pCTB8 was PCR-amplified from *H. pylori* 60190 DNA, using primers [(5' GTGAAAGCGAAAAACAAG 3')(SEQ ID NO:7) and (5' AAGAGAAGCTTTAAACCCTCC 3')(SEQ ID NO:8) ]. The km cassette from pILL600 (22,23) was ligated into the unique EcoRI site of pCTB8 to create pCTB8:km.

Throughout this application various publications are referenced by numbers within parentheses. The disclosures of these publications in their entireties are hereby incorporated by reference into this application in order to more fully describe the state of the art to which this invention pertains. The full citations for these publications are as follows:

REFERENCES

1. Altschul, S. F., W. Gish, W. Miller, E. W. Myers, and D. J. Lipman. 1990. Basic local alignment search tool. J. Mol. Biol. 215:403–410.
2. Biswas, G. D., J. Graves, R. Schwalbe, and P. F. Sparling. 1986. Construction of isogenic gonococcal strains varying in the presence of a 4.2-kilobase cryptic plasmid. J. Bacteriol. 167:685–694.
3. Devereux, J., P. Haeberli, and O. Smithies. 1984. A comprehensive set of sequence analysis programs for the VAX. Nucleic Acids Res. 12:387–395.
4. Feinberg, A. P. and B. Vogelstein. 1983. A technique for radiolabeling DNA restriction endonuclease fragments to high specific activity. Anal. Biochem. 132:6.
5. Gish, W. and D. J. States. 1993. Identification of protein coding regions by database similarity search. Nature Genetics. 3:266–72.
6. Hanahan, D. 1983. Studies on transformation of *Escherichia coli* with plasmids. J. Mol. Biol. 166:557.
7. Kraft, R., J. Tardiff, K. S. Krauter, and L. A. Leinwand. 1988. Using mini-prep plasmid DNA for sequencing double stranded templates with Sequenase. Biotechniques. 6:544–546.
8. Labigne-Roussel, A., P. Courcoux, and L. Tompkins. 1988. Gene disruption and replacement as a feasible approach for mutagenesis of *Campylobacter jejuni*. J. Bacteriol. 170:1704–1708.
9. Perez-Perez, G. I. and M. J. Blaser. 1987. Conservation and diversity of Campylobacter pyloridis major antigens. Infect. Immun. 55:505–513.
10. Perez-Perez, G. I., A. Z. Olivares, T. L. Cover, and M. J. Blaser. 1992. Characteristics of *Helicobacter pylori* variants selected for urease deficiency. Infect. Immun. 60:3658–3663.
11. Roca, A. I. and M. M. Cox. 1990. The RecA protein: structure and function. [Review]. Crit Rev Biochem Mol Biol. 25:415–56.
12. Sambrook, J., E. F. Fritsch, and T. Maniatis. 1987. Molecular Cloning: A laboratory manual, pages. Second edition, ed.; Cold Spring Harbor Lab., Cold Spring Harbor, N.Y.
13. Sanger, F., S. Nicklen, and A. R. Coulson. 1977. DNA sequencing with chain terminating inhibitors. Proc. Natl. Acad. Sci. USA. 74:5463–5467.
14. Schleif, R. F. and P. C. Wensink, 1981. Practical methods in molecular biology. 98–105. In: Springer Verlag, N.Y.
15. Segal, E. D. and L. S. Tompkins. 1993. Transformation of *Helicobacter pylori* by electroporation. BioTechniques. 4:225–226.
16. Staden, R. 1982. Automation of the computer handling of gel reading data produced by the shotgun method of DNA sequencing. Nucleic Acids Res. 10:4731–4751.
17. Story, R. M., D. K. Bishop, N. Kleckner, and T. A. Steitz. 1993. Structural relationship of bacterial RecA proteins to recombination proteins from bacteriophage T4 and yeast. Science. 259:1892–1896.
18. Yao, R., R. A. Alm, T. J. Trust, and P. Guerry. 1993. Construction of new Campylobacter cloning vectors and a new mutational cat cassette. Gene.
19. Young, R. A. and R. W. Davis. 1983. Efficient isolation of genes by using antibody probes. Proc. Natl. Acad. Sci. USA. 80:1194–1198.
20. Cover, T. L., and Blaser, M. J. (1992) Annu. Rev. Med. 43, 135–145.
21. Correa, P. (1992) Cancer Res. 52, 6735–6740.

22. Hentschel, E., Brandstatter, G., Dragosics, B., Hirschl, A. M., Nemec, H., Schutze, K., Taufer, M., and Wurzer, H. (1993) N. Engl. J. Med. 328, 308–312.
23. McKnight, S. L. and R. Kingsbury (1982) Transcriptional control signals of a eukaryotic protein-coding gene. Science 217:316.
24. Kunkel, T. A. (1985) Rapid and efficient site-specific mutagenesis without phenotypic selection. Proc. Natl. Acad. Sci. 82:488.
25. Eaton, J. A., C. L. Brooks, D. R. Morgan, and S. Krawowka (1991). Essential role of urease in pathogenesis of gastritis induced by *Helicobacter pylori* in gnotobiotic piglets. Infect. Immun. 59:2470–5.
26. Eaton, K. A., D. R. Morgan and S. Krakowka (1992) Motility as a factor in the colonisation of gnotobiotic piglets by *Helicobacter pylori*. J. Med. Microbiol. 37:123–7.

---

What is claimed is:

1. An isolated nucleic acid encoding a portion of the *Helicobacter pylori* recombinase consisting of the nucleotide sequence defined in the Sequence Listing as SEQ ID NO:1.

2. The nucleic acid of claim 1 in a vector suitable for expressing of the nucleic acid.

3. The nucleic acid of claim 2 in a host cell suitable for expressing the nucleic acid encoding the recombinase.

4. An isolated nucleic acid that selectively hybridizes with the nucleic acid of claim 1 under stringent conditions and has at least 70% complementarity with segment of SEQ ID NO:1 to which it hybridizes.

5. The nucleic acid of claim 4 in a vector suitable for expressing the nucleic acid.

6. The nucleic acid of claim 4 in a host cell suitable for expressing the nucleic acid.

* * * * *